United States Patent [19]

Assarsson et al.

[11] Patent Number: 4,578,353

[45] Date of Patent: * Mar. 25, 1986

[54] FERMENTATION OF GLUCOSE WITH RECYCLE OF NON-FERMENTED COMPONENTS

[75] Inventors: Per G. Assarsson, Toronto; Joseph H. Nagasuye, Mississauga, both of Canada

[73] Assignee: St. Lawrence Reactors Limited, Mississauga, Canada

[*] Notice: The portion of the term of this patent subsequent to Feb. 5, 2002 has been disclaimed.

[21] Appl. No.: 697,395

[22] Filed: Jan. 30, 1985

Related U.S. Application Data

[63] Continuation-in-part of Ser. No. 399,228, Jul. 19, 1982, Pat. No. 4,497,896.

[51] Int. Cl.$^4$ ............................ C12P 7/06; C12P 7/10
[52] U.S. Cl. ..................................... 435/161; 435/165; 127/36
[58] Field of Search ............... 435/161, 162, 163, 165; 127/36

[56] References Cited

U.S. PATENT DOCUMENTS

| | | | |
|---|---|---|---|
| 2,342,330 | 2/1944 | Christensen | 435/161 |
| 2,529,131 | 11/1950 | Boinot et al. | 435/162 |
| 4,155,884 | 6/1979 | Hughes | 260/9 |
| 4,221,609 | 9/1980 | Hughes | 127/38 |
| 4,287,303 | 9/1981 | Dahlberg et al. | 435/165 |
| 4,356,266 | 10/1982 | Muller et al. | 435/162 |
| 4,361,651 | 11/1982 | Keim | 435/161 |
| 4,421,856 | 12/1983 | Muller et al. | 435/161 |

Primary Examiner—Raymond Jones
Assistant Examiner—Marianne M. Cintins
Attorney, Agent, or Firm—Wegner & Bretschneider

[57] ABSTRACT

A process is described for producing a fermentation product such as ethanol, in which a feedstock is formed consisting of a slurry of starch and acid combined with a recycle stream of non-fermented carbohydrate material from a fermenter. This combined feedstock at a solids content of 15 to 30% is hydrolyzed in a single continuous hydrolyzer of a high intensity type to form a hydrolyzate in fluid form containing at least 80% glucose. The hydrolyzate is fermented to form a fermentation product and the fermentation product is distilled, leaving a distillation residue containing non-fermented carbohydrate material. This distillation residue forms the recycle stream and a substantial proportion of the non-fermented material is hydrolyzed together with the starch in a single hydrolysis stage to a fermentable glucose-containing fluid.

9 Claims, 5 Drawing Figures

FERMENTATION OF GLUCOSE WITH RECYCLE OF NON-FERMENTED COMPONENTS

This application is a continuation-in-part of application Ser. No. 399,228, filed July 19, 1982, now U.S. Pat. No. 4,497,896.

BACKGROUND OF THE INVENTION

This invention relates to the fermentation of fermentable sugars and, more particularly, to the fermentation of mono- and disaccharides produced by acid hydrolysis of carbohydrate material, preferably with recycle of non-fermented components from the fermentation back through the acid hydrolysis.

There exists in the world today an enormous demand for liquid fuels and this is being supplied almost entirely by distilled petroleum oils. It is, of course, well known that petroleum is a non-renewable resource and that finite supplies of this fuel source exist. As a result, there is now a very active search for alternative liquid fuels or fuel extenders.

Liquid fuels based on renewable resources which have considerable potential are alcohols. For instance, ethanol can be produced from almost any material which either exists in the form of, or can be converted into, a fermentable sugar. There are many natural sugars available for fermentation, but carbohydrates such as starch and cellulose can be converted into fermentable sugars which then ferment into ethanol.

Starch is, of course, one of the world's most abundant renewable raw materials and one answer would be to convert this very abundant material at low cost into fermentable sugars as feedstock for fermentation to ethanol. The fermentable sugars obtained from starch are glucose and maltose and these are typically obtained from the starch by hydrolysis, e.g. acid hydrolysis or enzyme hydrolysis. Most hydrolysis techniques which have been available have tended to be very expensive in terms of producing a feedstock for large scale alcohol production. There have been very significant improvements in the recent years in the hydrolysis of starch, particularly the continuous process described in Hughes, U.S. Pat. No. ,4,155,884. Such processes are highly economical and are well adapted for producing fermentable substrates of up to 92% fermentables or higher. Of course, in terms of maximizing ethanol production from a starch raw material source, it is desirable to have the fermentables as high as possible in the fermentation substrate.

With the typical known systems for producing ethanol from starch, e.g. using a dual enzyme system for liquifying and saccharifying the starch to glucose followed by batch fermentation, total processing times of 60 to 80 hours are usual. Fermentation times of 50 to 70 hours are commonplace. Such long total residence times result in enormous tankage requirements within the processing system when large scale ethanol production is contemplated.

In Boinot et al, U.S. Pat. No. 2,529,131 there is described a process for converting unfermentable materials into fermentable materials by acid hydrolysis. However, for their procedure to work it was necessary that the acid hydrolysis be carried out at such a high dilution that any tendency for the production of reversion products is avoided. This was accomplished by having a concentration of sugars in the unfermentables at no more than about 3% of the weight of the liquid to be treated.

U.S. Pat. No. 4,421,856, issued Dec. 20, 1983, describes a process in which stillage containing non-fermentable carbohydrate is recycled, but in this system the recycle is mixed with a hydrolyzate from a first stage hydrolysis and the mixture of non-fermentable carbohydrate and fermentable hydrolyzate is processed in a second stage hydrolysis. The content of non-fermentable sugar in the feed to the second stage hydrolysis was approximately 11% by weight.

SUMMARY OF THE INVENTION

According to this invention it has been discovered that when a fermentable substrate obtained by acid hydrolysis of starch or other carbohydrate is fermented, the non-fermented carbohydrate residue which is left after fermentation can be recycled to the starch hydrolysis stage and converted by hydrolysis into glucose. The unfermented residues simply pass through the fermenter without fermenting and after the fermentation and distillation, the non-fermented materials in the distillation residue are conveniently recycled as part of the feedstock to the hydrolysis stage.

While the process of this invention is particularly valuable for the production of ethanol, it can also be used to make other fermentation products derived from carbohydrates, such as glycerol, etc. The fermentation substrate (glucose-containing solution) can be produced by an inexpensive continuous acid-hydrolysis process, and even though this fermentation substrate may contain a substantial amount, e.g. up to 12% of carbohydrate material which does not ferment, it is not lost material because it can be recovered and re-hydrolyzed. Of course, it is desirable to keep the fermentables in the substrate as high as possible. With the recycle process of this invention, the actual amount of unfermented carbohydrate residue can be reduced to a very small amount while retaining all of the advantages of a very inexpensive process for producing the fermentable substrate.

Moreover, the total processing time from starch to ethanol is greatly decreased with the process of this invention to as little as 4 to 10 hours. This is in part dependent on the yeast concentration and concentration of fermentables and is also influenced by the fact that with the recycle system of this invention, the fermentation need only be continued until the readily fermentable materials have fermented and the fermentable materials which ferment slowly can form part of the recycle. Particularly where the continuous hydrolysis is combined with continuous fermentation, there is a very significant decrease in the process tankage requirements within the processing system to produce a given quantity of alcohol.

The starting material for the process of the present invention may be a carbohydrate material selected from the group consisting of unmodified carbohydrate material, chemically modified carbohydrate material, derivatized carbohydrate material and mixtures thereof. The most common such material is starch, e.g. corn, potato, tapioca, sago, rice, wheat, waxy maize, grain, sorghum and waxy sorghum. The starch can be used in refined form or as a natural component in cereal grains. It is also possible to use a cellulose containing material, for example, the hull fibers isolated in the wet-milling industry.

In order to produce glucose from the above materials, a slurry of the carbohydrate material is continuously moved through a confined tubular preheat zone and heat is rapidly transferred to the slurry in the tubular zone whereby it passes through a gellation stage and forms into a hot free-flowing fluid having a temperature of at least 125° C. The hot fluid thus formed is then immediately forced through a restrictive opening and into a confined tubular reaction zone accompanied by a sudden decrease in pressure whereby the carbohydrate material is made highly reactive. This highly reactive material is continuously moved, together with an acid, through the tubular reaction zone to produce a glucose containing fluid. This fluid should contain at least 80% glucose and preferably at least 85% glucose and is typically produced within a residence time of less than about 3 minutes within the pre-heat and reaction zones. It may also contain other hydrolysis products such as dimers and trimers as well as other reaction products.

The slurry of carbohydrate material being hydrolyzed should contain about 15% to 30%, preferably about 18% to 23%, carbohydrate solids. At solids levels above 25%, the glucose content of the hydrolysis product drops below desirable levels, while at solids levels below 15%, product distribution and dilution become a problem. The best results are obtained at a solids content of about 18% to 23%. Typical plant starch streams contain about 30-40% by weight, more commonly about 38-40%, starch solids and the recycle stream according to the invention also serves as a diluent, bringing the solid content of the combined feed slurry down to the desired range of 18 to 23%.

It is particularly noteworthy that the process of this invention requires only a single hydrolysis stage to hydrolyze both the starch and the recycled non-fermented sugars from the fermentation stage. In the processes of the prior patents, the non-fermented sugars could be hydrolyzed only at a solids content of no more than about 3% by weight. As a consequence, a separate hydrolysis stage at this low solids content was necessary.

With the process of the present invention, not only is the second hydrolysis stage not required, but it can be operated at a solids content in the process stream which not only optimizes fermentable sugar production in the hydrolysis stage, but also produces a fermentable sugar stream having a sugar concentration very close to that required for fermentation.

The fermentable substrate produced in the process of this invention can be fermented using yeasts or other ethanol-producing organisms. Either a regular yeast or a settling yeast and with both high and low yeast loadings may be used. It is also well adapted for either a continuous or batch system. The continuous system may be a single tank arrangement or a multi-tank (cascade) system. A variety of batch systems may also be used, including the normal batch system, the accelerated batch system and the fed batch system.

A wide variety of yeasts can be used for the fermentation, but the yeast most commonly used is *Saccharomyces cerevisiae*. Many different strains of *S. cerevisiae* are commercially available and these may differ in the amount of ethanol which they can tolerate, in the rate of fermentation which they can achieve and the type of saccharides they can ferment.

The best ethanol yields are generally obtained with a pH of about 4.5 to 4.7 at the start of the fermentation and a temperature between about 25° C. and 40° C. Most yeasts grow well on a variety of amino acids, amines, purines and pyrimidines as the source of nitrogen. Most natural sources of starch contain sufficient quantities of these nutrients to satisfy the growth requirements of the yeast.

When the carbohydrate starting material is a ground cereal grain, such as ground corn, the hydrolysis product may contain fibre, protein, etc. These residues may be removed prior to fermentation or may be simply left in the fermentation substrate through the fermentation. A particular feature of hydrolyzing ground cereal grains is that much of the fibrous material in the grain hydrolyzes to low sugars. For example, a typical ground corn contains about 70% starch, 9.5% protein, 4.5% fats, 1.5% ash, 2% sugars and 12% fibres.

The fibers are typically cellulose, hemi-cellulose and other non-starch carbohydrates. About 70% of these fibers hydrolyze to low sugars, thereby yielding additional monosaccharides. These additional sugars include glucose, xylose and arabanose. The result is that when ground cereal grains are used as the starting material, additional sugar for fermentation is obtained from the fibrous part of the cereal grain.

In a typical situation, a hydrolyzate produced by continuous acid hydrolysis of corn starch according to this invention contains about 85-90% glucose, with the balance being primarily dimers, along with trimers and other reaction products. This material, after adjustment of pH and dilution, becomes a fermentable feedstock to a fermentation system of known type. The fermentation product contains ethanol and this is distilled to separate the ethanol from the remaining components, leaving a stillage containing dimers, trimers, other hydrolysis products, glycerol and biomass. These materials all represent non-fermented components and represent a loss of yield from the carbohydrate feedstock.

When this stillage material is recycled as feed to the hydrolysis stage, it has surprisingly been found that, in particular, much of the dimers and trimers are hydrolyzed to glucose so that there is obtained in the hydrolysis stage a hydrolyzate material containing mainly glucose, along with small amounts of dimers, trimers, glycerol and biomass. This material then becomes an additional fermentable substrate which proceeds to the fermentation stage together with the fermentable substrate obtained from the original corn starch feedstock.

BRIEF DESCRIPTION OF THE DRAWINGS

Certain preferred embodiments of the present invention are illustrated in the attached drawings in which:

FIG. 5 is a graph showing hydrolysis and fermentation of corn starch using the process of this invention.

DETAILED DESCRIPTION

Figures 1, 2:
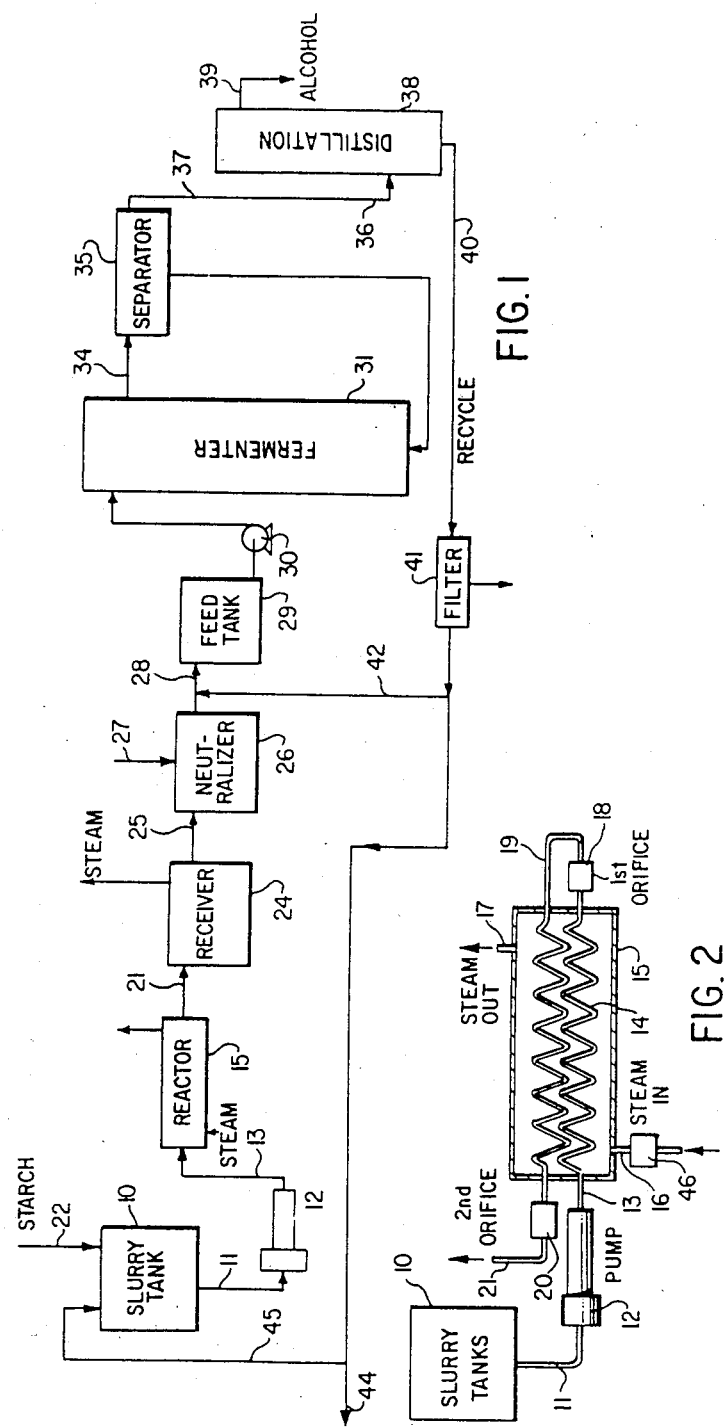
FIG. 1 is a schematic flow sheet of one preferred embodiment of the entire process sequence.
FIG. 2 is a schematic representation of a hydrolyzer for producing glucose.
Figure 3:
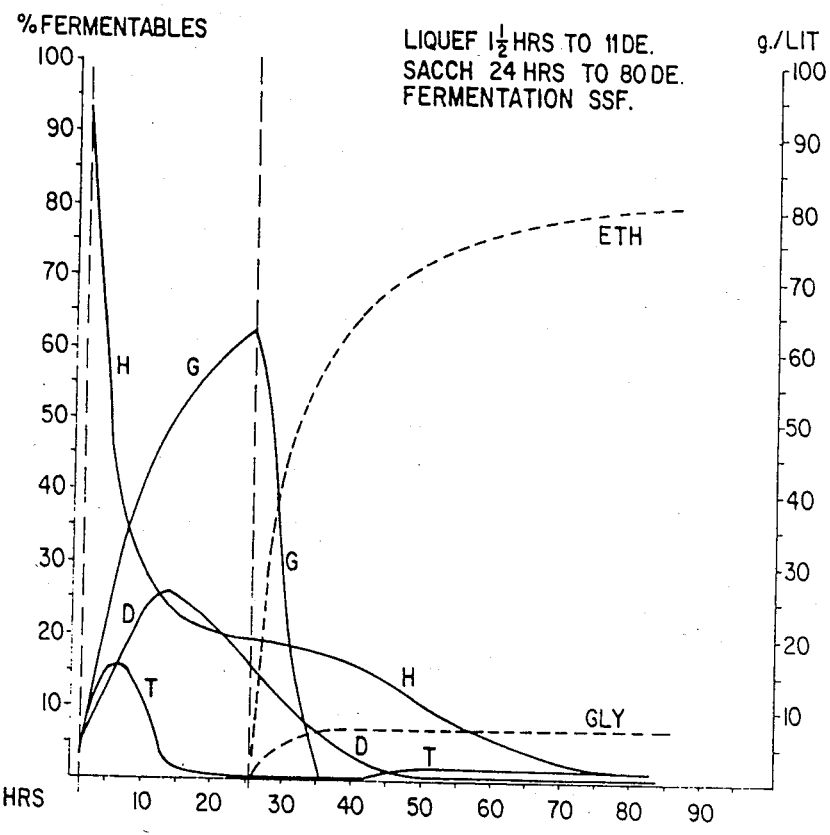
FIG. 3 is a graph showing hydrolsis and fermentation of corn starch using dual enzyme hydrolysis and SSF fermentation.
Figure 4:
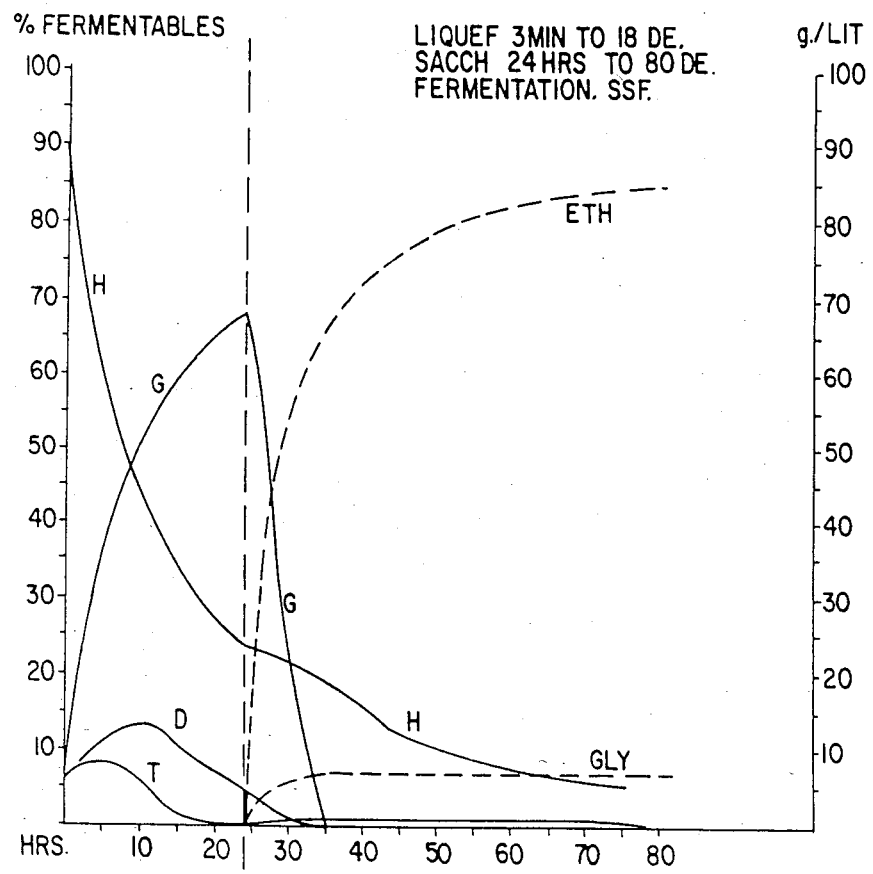
FIG. 4 is a graph showing hydrolysis and fermentation of corn starch using acid/enzyme hydrolsis and SSF fermentation.

A holding tank 10 is provided for a starch slurry feed, this starch slurry being received through line 22. The holding tank has an outlet line 11 which feeds to a positive displacement pump 12. The slurry is pumped from pump 12 to line 13 at high pressure and into a heating tube 14. The pressure within the tube 14 may be controlled by varying the speed of the pump 12.

The main reactor of this apparatus is a closed and insulated vessel 15 which is essentially a steam vessel being supplied by a steam inlet line 16 and a steam outlet line 17. A steam control valve 46 is provided in the steam inlet line.

The tube 14 is made of corrosion resistant steel. This is the preheater for the reaction and the slurry passing through tube 14 passes through a gell stage and forms into a hot free-flowing liquid. The outlet of preheat tube 14 feeds into a first restrictive opening or orifice 18 having a much smaller diameter than the diameter of tube 14. The outlet of the orifice 18 connects to a further stainless steel tube 19 which forms the tubular reaction zone. This tube passes back through the steam vessel 15 or a separate heater and the reaction occurs during the travel of the hot liquid through tube 19.

In order to control the pressure within tube 19, a second restrictive opening or orifice 20 is provided at the outlet. The reaction product is then collected through outlet line 21. Further details of the above apparatus are described in Assarsson and Nagasuye, U.K. patent application Publication Ser. No. 2057478, published Apr. 1, 1981.

The product which is obtained through line 21 is a glucose containing liquid and it goes into receiving tank 24. The receiving tank may also be a cooling heat recovery system in which the steam is flashed off and heat is recovered from the hot glucose product while bringing the glucose down to a fermentation temperature in the order of about 30° C. From this receiving tank it is pumped via line 25 into a mixer 26 where the pH is adjusted. Here the glucose containing liquid is neutralized by addition of neutralizing agent 27 to a proper pH for fermentation. The neutralized liquid is moved via line 28 to a feed tank 29 for the fermenters. From this tank the glucose is pumped via pump 30 into a fermentation system 31.

The fermented product emerges from the fermenter 31 via outlet line 34 and into a solids/liquid separator 35. Here a top stream 37 is removed which is primarily ethanol and water and a bottom stream 36 containing yeast is recycled into the bottom of the fermenter 31.

The fermentation product containing ethanol is carried via line 37 to a distillation column or beer still 38 in which substantially pure ethanol is distilled off via outlet line 39 and the stillage is removed from the bottom of the distillation column via line 40. This stillage contains some dimers, trimers and other carbohydrates as well as some glycerol and biomass. These are all non-fermented materials and represent a potential loss of yield from the original feedstock.

The stillage is pumped through a filter 41 where solids are removed as a sludge and the liquid continues as a recycle stream. One portion is recycled via line 42 back to the fermenter feed tank 29 and this is used to maintain a material balance within the system. The remainder of the reycle stream travels via line 43 with part of this stream being discharged at 44 and the remainder being recycled via line 45 into the hydrolysis feed tank 10. The recycle through line 45 serves the additional purpose of diluting a plant stream 22 containing about 38–40% starch solids down to a suitable processing level.

The following examples are further illustrative embodiments of this invention. All parts and proportions are by weight unless otherwise specified and all pressures are guage pressures.

EXAMPLE 1

A fermentation substrate was prepared using a reactor of the type described in FIG. 2. The tubes 14 to 19 were made from ½ inch I.D. stainless steel tubing with tube 14 having a length of 80 feet and tube 19 having a length of 280 feet. The first orifice had a diameter of 0.062 inch and the second orifice was in the form of a pair of adjacent openings each having a diameter of 0.062 inch.

A starch slurry was formed from starch and water, this slurry containing 20% starch solids. 950 mls of 31% hydrochloric acid were added to the slurry per 100 lbs. of starch solids and this gave the slurry a conductivity of 13,000 micromhos at 30° C. This slurry passed through the reactor at a rate of 1.6 gallons per minute under the following reaction conditions.

TABLE 1

| REACTOR CONDITIONS: | |
|---|---|
| Temperatures | |
| Steam supply | 167° C. |
| Steam after control valve | 167° C. |
| Steam bath (bottom) | 166° C. |
| Steam bath (top) | 166° C. |
| 1st orifice inlet | 158° C. |
| 1st orifice outlet | 158° C. |
| 2nd orifice inlet | 165° C. |
| Pressures | |
| Steam supply | 620 kPa |
| Feed pump outlet | 3654 kPa |
| 1st orifice inlet | 3447 kPa |
| 1st orifice outlet | 2068 kPa |

The hydrolyzate obtained had a pH of about 1.5 and contained about 86.11% glucose, 9.72% dimers, 1.03% trimers and 3.14% other carbohydrates on a dry solids basis. This product was then neutralized to pH 4.6, then diluted to about 20% sugar by weight and subjected to fermentation.

The fermentation was carried out in a batch fermenter using Bakers' yeast (S. Cerevisiae var. diastaticus) in an amount of 24 g. dry wt./liter of substrate. The fermentation was conducted at 30° C. for about 16 hours.

The resulting fermentation product contained on a dry weight basis 9.25% dimers, 1.29% trimers, 4.34% other carbohydrates, 4.13% glycerol and 37.89% ethanol. The yeast was filtered out and the ethanol distilled off leaving a stillage consisting 11.25% dimers, 1.29% trimers, 4.28% other carbohydrates and 4.13% glycerol on a dry weight basis. This material was then used as a feedstock to the continuous hydrolyzer described in FIG. 2 under the same conditions as described above and from this hydrolysis there was obtained a solution containing 14.56% glucose, 0.61% dimers, 0.06% trimers, 2.06% other carbohydrates, 3.65% glycerol on a dry solids basis.

This glucose product was then fermented under the same conditions as described above to obtain a fermentation product containing 0.47% dimers, 0.05% trimers, 1.40% other carbohydrates, 4.44% glycerol, 6.87% ethanol. Thus a further 6.87% was recovered from the original starch feedstock by the recycle sequence. The final result of the combined two stages was to produce a product containing on a dry weight basis, 0.47% dimers, 0.05% trimers, 1.40% other carbohydrates, 4.44% glycerol and 44.76% ethanol. It will further be seen that only 1.92% of the original feedstock represent unfermented material with the system of the present invention.

EXAMPLE 2

Using the same hydrolysis reactor as in Example 1 and the same conditions, a hydrolyzate was obtained containing 88.92% glucose, 10.03% dimers and 1.05% trimers. This product was then neutralized to about pH 4.6, diluted to about 20% sugar by weight and subjected to fermentation.

The fermentation was carried out in a batch fermenter using bakers yeast in an amount of 24 g. dry wt./liter of substrate. The fermentation was conducted at 30° C. for about 23 hours.

The resulting fermentation product contained 9.55% dimers, 1.33% trimers, 4.26% glycerol and 39.13% ethanol. There was no residual glucose. The yeast was filtered out and the ethanol was distilled off, leaving a stillage containing 9.55% dimers, 1.33% trimers and 4.26% glycerol. This material formed a recycle stream which was split into streams A and B in the ratio A:B of 2:1. Stream B was sent to the wet milling stage, while stream A, containing 6.37% dimers, 0.89% trimers and 2.84% glycerol was recycled into the feed stock for the hydrolyzer.

A typical plant starch stream contains about 38-40% starch solids and the recycle stream serves as a diluent, diluting the starch stream down to about 20% starch solids. This mixed stream was then passed through the hydrolyzer providing a hydrolyzate containing 85.22% glucose, 12.16% dimers, 1.44% trimers and 1.19% glycerol. The hydrolyzate was then fermented in the same manner as above to give a product containing 11.58% dimers, 1.81% trimers, 5.65% glycerol and 40.13% ethanol. The ethanol was distilled off and the stillage was recycled.

We claim:

1. A process for producing fermentation products from carbohydrate material which comprises preparing an aqueous slurry feed of carbohydrate material, said slurry containing about 15-30% by weight of carbohydrate solids, continuously moving said slurry feed through a single hydrolysis stage in which the slurry feed is moved through a confined tubular preheat zone and sufficient heat is transferred to the slurry whereby it passes through a gelation stage and forms into a hot free flowing liquid and said hot liquid is immediately forced through a restrictive opening and into a confined tubular reaction zone accompanied by a sudden decrease in pressure at a rate sufficient that the carbohydrate material is made highly reactive, and continuously moving the highly reactive carbohydrate material, together with an acid hydrolyzing agent, through the tubular reaction zone to produce a hydrolyzate in fluid form containing at least 80% glucose, fermenting the glucose-containing fluid to form a fermentation product, distilling the fermentation product to separate the product from a distillation residue containing non-fermented carbohydrate materials, and recycling at least part of the obtained distillation residue containing non-fermented carbohydrate materials to form part of the slurry feed to said single hydrolysis stage whereby a substantial portion of said non-fermented materials is hydrolyzed to form part of said fermentable glucose-containing fluid.

2. A process according to claim 1 wherein the product of fermentation is ethanol.

3. A process according to claim 2 wherein the carbohydrate is starch or a starch-containing material.

4. A process according to claim 3 wherein the feed slurry contains about 18-23% by weight of carbohydrate solids.

5. A process according to claim 4 wherein the hydrolysis is conducted to form a hydrolyzate containing at least 85% glucose.

6. A process according to claim 3 wherein the recycled distillation residue is mixed as a diluent with a starch-containing feed slurry having a starch solids content of about 30-40% by weight to form the feed slurry containing about 18-23% by weight of starch solids.

7. A process according to claim 6 wherein the recycled distillation residue is mixed with a starch-containing slurry containing about 38-40% by weight starch solids.

8. A process according to claim 4 wherein a hydrolyzate containing at least 85% glucose is formed within about 3 minutes in the hydrolysis stage.

9. A process according to claim 3 wherein the starch-containing material is ground cereal grain, and the product of the hydrolysis stage is a hydrolyzate in fluid form containing glucose together with fibre, protein and other residues from the cereal grain.

* * * * *